United States Patent [19]

Kraiselburd

[11] Patent Number: 5,470,572
[45] Date of Patent: Nov. 28, 1995

[54] NON-INFECTIOUS SIMIAN IMMUNODEFICIENCY VIRUS PARTICLES PRODUCED BY CELL LINE CRL 11393

[75] Inventor: Edmundo Kraiselburd, Santurce, Puerto Rico

[73] Assignee: University of Puerto Rico, San Juan, Puerto Rico

[21] Appl. No.: 93,336

[22] Filed: Jul. 16, 1993

[51] Int. Cl.$^6$ .............................. A61K 39/21; C12N 7/00; C12N 5/10; C07K 14/155

[52] U.S. Cl. .................................... 424/208.1; 424/184.1; 424/188.1; 424/204.1; 424/205.1; 424/207.1; 435/69.3; 435/235.1; 435/236; 435/237; 435/240.1; 435/240.2; 514/2

[58] Field of Search .............................. 424/88, 89, 93 T, 424/184.1–188.1, 204.1, 207.1–208.1, 205.1; 435/69.3, 235.1, 236, 237, 240.1, 240.2, 252.3; 514/2

[56] References Cited

U.S. PATENT DOCUMENTS

4,752,565  6/1988  Folks et al. .................................. 435/5

FOREIGN PATENT DOCUMENTS

9015141  12/1990  WIPO .
WO91/05864  5/1991  WIPO .
WO91/19785  12/1991  WIPO .

OTHER PUBLICATIONS

Hernandez, S. et al. Symp. Nonhum. Primate Models AIDS abstract No. 87, (Nov. 1992).
Desrosiers, R. C. et al. Proc. Natl. Acad. Sci. USA 86: 6353–6357 (1989).
Marx, P. A. et al. J. Virol. 65(8): 4480–4485 (1991).
Norley, S. et al. Immunobiol. 184: 193–207 (1992).
Cohen, J. Science 262: 980–81 (1993).
E. Kraiselburd, et al., Characterization of Biologically Cloned CEMX174 Cells Expressing Non–Infectious SIV$_{sm}$ Particles *IXth International Conference on AIDS, Berlin* Abstract PO–A33–0798, Jun. 6–11, (1993).
P. R. Johnson et al. Inactivated whole–virus vaccine derived from a proviral DNA clone of simian immunodeficiency virus induces high levels of neutralizing antibodies and confers protection against heterologous challenge *Proc. Natl. Acad. Sci. USA*, 89, 2175–2179 (1992).
J. A. Hoxie et al., Biological Characterization of a Simian Immunodeficiency Virus–Like Retrovirus (HTLV–IV): Evidence for CD4–Associated Molecules Required for Infection *Journal of Virology* 62, 2557–2568 (1988).
E. Kraiselburg et al.; Biochemical and Biological properties of SIV–chronically infected cells *VIII International conference on AIDS, Amsterdam* Jul. 19–24, 1992.
R. E. Benveniste et al.; Characterization of clones of HIV–1 Infected HuT 78 Cells Defective in gag Gene Processing and of SIV Clones Producing Large Amounts of Envelope Glycoprotein *J. Med. Primatol*, 19 pp. 351–366 (1990).
Hoxie, J. A. et al., "Persistent Noncytophatic Infection of Normal Human T–Lymphocytes with AIDS–Associated Retrovirus", *Science* 229:1400 (1985).
Folks, T. M. et al., "Induction of HTLV–III/LAV from a Nonvirus–Prodiucing T–Cell Line: Implications for Latency", *Science* 231:601 (1986).
Folks, T. M. et al., "Biological and Biochemical Characterization of a Cloned LEU–3 Cell Surviving Infection with the Acquired Immune Deficiency Syndrome Retrovirus", *J. Exp. Med.* 164240 (1986).
Folks, T. M. et al., "Characterization of Promonocyte Clone Chronically Infected with HIV and Inducible by 13–Phorbol–12–Myristate Acetate", *J. Immunol.* 140:1117 (1988).
Murphy–Corb, M. et al., "A Formalin–Inactivated Whole SIV Vaccine Confers Protection in Macaques", *Science* 246:1293 (1989).

Primary Examiner—Mary E. Mosher
Assistant Examiner—Michael S. Tuscan
Attorney, Agent, or Firm—Bell, Seltzer, Park & Gibson

[57] ABSTRACT

A cell line capable of producing SIV viral materials without producing infectious viral particles is disclosed. The SIV viral particles produced are immunogenic and non-infectious. The cell line and the products produced by the cell line are useful for diagnostic purposes and for immunization purposes.

15 Claims, 4 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

CTCTGCGGAG AGGCTGGC 18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

GGGTCCTAAC AGACCAGG 18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:3:

GATTGAGCCC TGGGAGGT 18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA (genomic)

(  i i i  ) HYPOTHETICAL: NO (  i v  ) ANTI-SENSE: NO (  x i  ) SEQUENCE DESCRIPTION: SEQ ID NO:4:

ACCAGGCGGC GACTAGGA 18

NON-INFECTIOUS SIMIAN IMMUNODEFICIENCY VIRUS PARTICLES PRODUCED BY CELL LINE CRL 11393

These studies were supported in part by the U.S. Government under NIAID Contract No. N01-AI-05057 and the NIH/MBRS grant GM08224-07. The government has certain rights in this invention.

FIELD OF THE INVENTION

The present invention relates to a cell line capable of generating non-infectious SIV viral particles, to the non-infectious particles so produced, and to compositions containing and methods of using the cells and the non-infectious particles.

BACKGROUND OF THE INVENTION

Simian immunodeficiency viruses (SIV) are a group of primate retroviruses that are morphologically and antigenically related to human immunodeficiency, viruses (HIVs). HIV infection in humans is associated with the development of Acquired Immune Deficiency Syndrome (AIDS). The SIV group includes strains isolated from macaques ($SIV_{mac}$) (see, e.g., Daniel et al., Science 228, 1201 (1985)); sooty mangabey monkeys ($SIV_{smm}$) (see, e.g., Lowenstein et al., Int. J. Cancer 38, 563–574, (1986)); African Green Monkeys ($SIV_{agm}$)(see, e.g., Otha et al., Int. J. Cancer 41, 115 (1988)); chimpanzees ($SIV_{cpz-ant}$) (PCT application WO 91/19785 published 26 Dec. 1991) and mandrills ($SIV_{mnd}$)(Tsujimoto et al., J. Virol. 62, 4044 (1988)). Macaques infected with cultured SIV develop opportunistic infections and other manifestations of immunodeficiency associated with a loss of CD4+ cells.

Both HIV and SIV replicate in vitro in a variety of $CD_4+$ cell lines and in primary cell cultures. Cellular infection causes drastic cytopathic effects and cytolysis. The cytopathic effects include syncytia formation, which is produced by the interaction of viral envelope glycoproteins (expressed on the surface of the infected cells) and uninfected cells that express $CD_4$.

HIV and SIV can also establish persistent infections in vitro. See, e.g., Benveniste et al., J. Med. Primatol., 19, 351 (1990); Lairmore et al. , Arch. Virol. 121, 43 (1991). Persistently infected cells can produce infectious as well as defective virus particles. HIV mutants defective in the pol region have been obtained from cultures. Folks et al., Science, 231, 601 (1986). Products of the pol virus genome region, including the virus protease enzyme, are required for viral infectivity. See, e.g., Henderson et al., J. Virol., 66, 1856 (1992); Henderson et al., J. Med. Primatol. 19, 411 (1990). A noninfectious HIV mutant able to synthesize all major viral proteins except proteins p64 and p34 is disclosed in U.S. Pat. No. 4,752,565 to Folks et al. A non-infectious mutant HIV virus lacking a functional protease, and a cell line infected with the mutant virus, is described in Benveniste et al., J. Med. Primatol., 19, 351 (1990). Mutant SIV strains producing large amount of either the envelope glycoprotein gp120 or the nucleic acid binding gag protein are described in Benveniste et al., J. Med. Primatol., 19, 351 (1990).

Additionally, a natural SIV isolated from chimpanzees has been reported as having antigenic properties closer to HIV-1 than HIV-2, and has been proposed for use in preparing antibodies for diagnostic kits and for developing vaccines against HIV-1. Published application, WPI Acc No: 90-329700/44.

Various strategies are currently being investigated in attempts to develop effective vaccines against retroviruses such as SIV and HIV, including subunit vaccines and live recombinant virus vaccines. Synthetic peptides containing multiple epitopes of a given pathogen are also under investigation for use in vaccines. See, e.g., PCT patent application WO 91/05864, international publication date 2 May 1991.

Inactivated whole-virus vaccines consist of purified preparations of intact viral particles that have been rendered non-infectious by chemical or physical methods. Inactivated SIV viral vaccines have been tested in macaques, and have resulted in the development of high levels of neutralizing antibodies. Johnson et al., Proc. Natl. Acad. Sci. USA, 89, 2175 (1992). While such vaccines are comparatively easy to produce and contain most or all of the important immunological epitopes, production of these vaccines requires the propagation of large amounts of infectious virus. Additionally, the virus must be rendered completely non-infectious without altering various immunological epitopes.

Because both SIV and HIV are spread by contaminated body fluids, immunochemical testing of sera can be used to determine whether animals or humans are infected with SIV or HIV. Immunochemical techniques employ proteins isolated from purified virus particles or infected cell lysates as antigens to detect serum antibodies directed against the virus of interest. These antigens may also be used in competition studies designed to detect the presence of viral antigens. Preparation of the viral proteins requires manipulating large volumes of virus and tissue cultures; if the virus is infectious workers are exposed to a risk of accidental infection.

SUMMARY OF THE INVENTION

A first aspect of the present invention is a cell line which produces non-infectious SIV viral particles, the cell line having the identifying characteristics of ATCC accession number CRL 11393.

A second aspect of the present invention is non-infectious SIV viral particles having the identifying characteristics of the non-infectious SIV viral particles produced by the aforementioned cell line.

A further aspect of the present invention is a composition of matter comprising an antigenic preparation of SIV viral particles having the identifying characteristics of the non-infectious SIV viral particles produced by the aforementioned cell line.

A further aspect of the present invention is a pharmaceutical composition comprising an immunogenic amount of SIV viral particles having the identifying characteristics of the SIV viral particles produced by the aforementioned cell line, in a pharmaceutically acceptable carrier.

A further aspect of the present invention is a kit for detecting the presence of SIV antibodies, which comprises a container containing an antigenic preparation of cells having the identifying characteristics of the aforementioned cell line, or viral particles produced by the cell line.

A further aspect of the present invention is a kit for detecting the presence of HIV type 2 (HIV-2) antibodies, which comprises a container containing an antigenic preparation of cells having the identifying characteristics of the aforementioned cell line, or viral particles produced by the cell line.

A further aspect of the present invention is a method for inducing antibodies to SIV, comprising administering an immunogenic amount of SIV viral particles having the identifying characteristics of the SIV viral particles produced by the aforementioned cell line.

A further aspect of the present invention is a method for immunizing a subject against infection by SIV, comprising administering to a subject an immunogenic amount of the SIV vital particles having the identifying characteristics of the SIV viral particles produced by the aforementioned cell line.

A further aspect of the present invention is a method for inducing antibodies to HIV-2, comprising administering an immunogenic amount of SIV viral particles having the identifying characteristics of the SIV viral particles produced by the aforementioned cell line.

A further aspect of the present invention is methods of determining the sensitivity of SIV proviral DNA detection assays, comprising using a preparation of cells having the identifying characteristics of the aforementioned cell line as a standard.

The foregoing and other objects and aspects of the present invention are explained in detail in the specification set forth below.

BRIEF DESCRIPTION OF THE FIGURES

FIG. 5: Electron microscopy of clone B7 cells.

DETAILED DESCRIPTION OF THE INVENTION

The aspects of the present invention are achieved by a cell line having the identifying characteristics of the deposit designated $SIV_{sm}B7$ cells, made in accordance with the provisions of the Budapest Treaty on Jun. 30, 1993, at the American Type Culture Collection, Rockville, Md., USA, and given the ATCC accession number CRL 11393.

Those skilled in the art will readily recognize that methods and materials similar or equivalent to those described herein can be used in the practice of the present invention; preferred methods and materials are described below. All publications mentioned herein are intended to be incorporated by reference; all U.S. patents cited herein are intended to be incorporated by reference in their entirely.

Described herein is a cell line derived from CEMX174 cells that survived infection with a mutant SIV. The cells of the present invention are capable of producing non-infectious viral particles and SIV viral antigens without concomitant production of infectious SIV virus. A non-infectious viral particle is herein defined as a defective virion which is incapable of infecting a host cell due to the presence of one or more genetic modifications or deletions of viral genes or other genetic elements which are functionally critical at some stage of the virus life cycle. Non-infectious viral particles may or may not contain all of the viral proteins normally found in infectious virions and may or may not contain RNA, however, if RNA is contained it is incapable of infecting host cells.

$SIV_{sm}$ chronically infected cultures were obtained by the present inventors by infecting CEMX174 cells with either of two strains of SIV ($SIV_{sm}H3$ and $SIV_{sm}/E660$). Single cell clones were derived from the resulting chronically SIV-infected CEMX174 cell cultures, and these clones were characterized for the ability to produce virus-specific proteins and infectious particles. It was found that non-infectious particles ($SIV_{sm}B7$) produced by a single cell clone ($SIV_{sm}B7$ cells) contained SIV envelope glycoproteins and large amounts of gag precursors and gag proteins, but lacked pol and vpx gene products. Defects in vpx production, and in the proteolytic processing of viral proteins, were evident in $SIV_{sm}B7$.

Western blot analysis, performed with either monoclonal or polyclonal sera, showed that the chronically infected $SIV_{sm}B7$ cells produced non-infectious viral particles which contained envelope proteins (gp135 and gp43), gag precursors, and gag proteins (p27, p16, and p8). However, these particles lacked detectable levels of vpx and integrase, and contained several fusion proteins which expressed viral protease antigens. These defective viruses failed to infect established $CD_4+$ cell lines, and failed to infect primary cultures of macrophages or peripheral blood lymphocytes obtained from humans and rhesus macaques. Lack of infection correlated with lack of viral DNA, as detected by polymerase chain reaction (PCR) amplification of genomic DNA extracted from cultures of $SIV_{sm}B7$. During more than one year of in vitro cultivation, no infectious virus was recovered from clone $SIV_{sm}B7$ cells. These cells produced stable, non-infectious virus mutants that contained env and gag proteins, but lacked detectable amounts of vpx and enzymes required for virus replication in tissue culture cells.

A composition of matter comprising an antigenic preparation of the non-infectious SIV viral particles produced by the cell line of the present invention is disclosed herein. This composition may include any pharmaceutically acceptable carrier (such as sterile, pyrogen-free physiological saline solution, or sterile, pyrogen-free phosphate-buffered saline solution). The SIV viral particles of the composition may be live, killed, fixed or lyophilized, as is most suitable for the intended use.

Purified viral particles or lysates of infected cells of the present invention may be combined with any suitable pharmaceutically acceptable carrier (such as sterile, pyrogen-free physiological saline solution, or sterile, pyrogen-free phosphate-buffered saline solution). The viral particles are included in an immunogenic amount, the amount to be determined by the intended use. The immunogenic activity of a given amount of the non-infectious viral particle of the present invention may be determined by any of a number of methods known in the art. The increase in titer of antibody against a particular SIV antigen upon administration may be used as a criteria for immunogenic activity.

The antigenic proteins produced by the cells of the present invention are useful as reagents in immunoassay diagnostic studies of retroviruses. Immunochemical methods for detecting retroviruses include, for example, immunofluorescence assays or immunoenzymatic assays. Immunofluorescence assays typically involve incubating, for example, serum from the subject to be tested with preparations of cells infected with the pathogenic virus. Immune complexes formed are detected using either direct or indirect methods, for example, the use of antibodies to which fluorescent labels such as rhodamine or fluorescein have been coupled. Immunoenzymatic assays typically involve viral extracts or other antigen-containing compositions bound to a surface. Serum from a subject to be tested for the presence of antibodies directed against one or more of antigens is contacted with the surface and, after a period of incubation, unbound substances are washed away. The presence of immune complexes is detected using antibodies labeled with an enzyme such as horseradish peroxidase, alkaline phosphatase, or beta-galactosidase, which is capable of converting a colorless or nearly colorless substrate into a highly colored product, or an enzyme which emits light in the presence of the proper substrate. The amount of product formed is detected visually, spectrophotometrically, or luminometrically, and is compared to a similarly treated control. The presence of antibodies in biological fluids may also be detected by agglutination. Viral lysates or antigen compositions are used to coat, for example, latex particles.

Diagnostic tests utilizing the present invention may be carried out in accordance with known techniques. Such techniques provide a method of detecting the presence of SIV by detecting the presence of SIV antibodies. Such methods comprise collecting an antibody-containing biological sample (e.g., blood, blood sera, blood plasma, cerebrospinal fluid, tissue samples) from the subject; contacting the sample with an antigenic preparation of the viral particles of the present invention as given herein, and then detecting the formation of a reaction product between the antibodies in the sample and the antigenic preparation. Any suitable assay format, such as radioimmunoassay (RIA) or enzyme-linked immunosorbent assay (ELISA) may be employed, in accordance with known techniques. See, e.g., Immunology: Basic Processes, 162–175 (J. Bellanti,(Ed.) 2d ed., W. B. Saunders Co., (1985).

Also disclosed herein are kits for the detection of SIV infection. Such kits comprise a container containing an antigenic preparation of the viral particles of the present invention, which may be lyophilized. The antigenic preparation may comprise the SIV external envelope protein (env) of $SIV_{sm}B7$, the transmembrane envelope (env) protein of $SIV_{sm}B7$, or the SIV group antigen (gag) protein of $SIV_{sm}B7$. The kits may also optionally include instructions, typically on a printed sheet contained within a package holding the container, or printed on the package itself, detailing the use of the elements of the kit for carrying out the methods described herein. The kits may also optionally be sterile.

Also disclosed herein are kits for detecting HIV-2 infection, using the diagnostic methods for SIV described above. Viruses of the SIV family show 80–90% homology to those of the HIV-2 family. Benveniste et al., J. Virol. 60, 483–490, (1986); Desrosiers et al., *AIDS Res. Human Retroviruses*, 5, 465 (1989). Such kits comprise a container containing an antigenic preparation of the cells of the present invention. The antigenic preparation may comprise the SIV external envelope protein (env) of $SIV_{sm}B7$, the transmembrane envelope (env) protein of $SIV_{sm}B7$, or the SIV group antigen (gag) protein of $SIV_{sm}B7$. The sample to be tested for the presence of HIV-2 antibodies is contacted with the antigenic preparation so that a reaction product may be formed between the HIV-2 antibodies and the SIV antigens. This reaction product is then detected with any suitable detection step. The kits may also optionally include instructions, typically on a printed sheet contained within a package holding the container, or printed on the package itself, detailing the use of the elements of the kit for carrying out the methods described herein.

A method of inducing antibodies to SIV in a subject, as disclosed herein, comprises administering to a subject an immunogenic amount of non-infectious SIV vital particles of the present invention. This method may be used to make polyclonal or monoclonal antibodies, which may be used in diagnostic assays. Suitable subjects include mammals (such as, for example, rats, rabbits, mice, and horses) and primates. The term primates is herein intended to encompass any members of the order Primata (for example, lemurs, mandrills, rhesus monkeys, macaques, and chimpanzees) and to include humans. Suitable subjects include those susceptible to SIV infection as well as those not susceptible to SIV infection but in whom antibodies to SIV may be raised (e.g., rabbit, horse). Humans are known to be susceptible to SIV infection.

The antibodies induced by the above method can be neutralizing or non-neutralizing antibodies. If the method is to be used for conferring protection from SIV infection, the antibodies must be neutralizing and the subject must be susceptible to SIV infection. When the above methods are used for raising antibodies to be used for diagnostic or other uses, the antibodies need not possess neutralizing activity, and the subjects in which the antibodies are raised need not be susceptible to SIV infection.

A method of inducing antibodies to HIV-2 in a subject, as disclosed herein, comprises administering to a subject an immunogenic amount of non-infectious SIV vital particles of the present invention. Antibodies to SIV are known to react to HIV-2, due to the high homology between the two viruses. Suitable subjects include mammals (such as, for example, rabbits, mice, and horses) and primates. The term primates is herein intended to encompass any members of the order Primata (for example, lemurs, mandrills, rhesus monkeys, macaques, and chimpanzees) and to include humans. Suitable subjects include those susceptible to HIV-2 infection as well as those not susceptible to HIV-2 infection but in whom antibodies to SIV may be raised.

In the above methods of inducing antibodies, viral particles of the present invention may be combined with any suitable pharmaceutically acceptable carrier (such as sterile, pyrogen-free physiological saline solution, or sterile, pyrogen-free phosphate-buffered saline solution). The viral particles are included in an effective immunogenic amount. The precise amount to be administered to a given subject is determined by techniques known in the art, and will vary depending on the route of administration, the subject and the desired response. Administration to the subject may occur by any suitable route (e.g., by intramuscular injection, subcutaneous injection, intraperitoneal injection, or intravenous injection). The appropriate immunogenic dosage will depend upon the particular subject and the desired outcome. Techniques to determine a particular immunogenic amount of the viral particles of the present invention will be apparent to those of ordinary skill in the art. See e.g., Johnson et al., *Proc. Natl. Acad. Sci. USA* 89, 2175, (1992). For example, the active agent (viral particles or preparations thereof) may be given in an amount of from 0.05 to 50 µg per Kg body weight (e.g., 0.5 or 1.0 µg per Kg).

A method of immunizing a subject susceptible to SIV infection, as disclosed herein, comprises administering to a subject an immunogenic amount of noninfectious SIV viral particles of the present invention, such that the subject is rendered immune to infection by SIV. Suitable subjects and methods are as described above in connection with methods of inducing antibodies.

The presence of SIV proviral DNA in cells or tissues can be ascertained by a variety of known techniques. Many methods are known for the amplification of a selected, or target, nucleic acid sequence. See generally D. Kwoh and T. Kwoh, *Am. Biotechnol. Lab.* 8, 14–25 (1990). Examples of amplification techniques include, but are not limited to, polymerase chain reaction (PCR), ligase chain reaction, strand displacement amplification, transcription-based amplification (see D. Kwoh et al., *Proc. Natl. Acad Sci. USA* 86, 1173–1177 (1989)), self-sustained sequence replication (or "3SR")(see J. Guatelli et al., Proc. Natl. Acad. Sci. USA 87, 1874–1878 (1990)), the Qβ replicase system (see P. Lizardi et al., *BioTechnology* 6, 1197–1202 (1988)), nucleic acid sequence-based amplification (or "NASBA")(see R. Lewis, *Genetic Engineering News* 12 (9), 1 (1992)), the repair chain reaction (or "RCR")(see R. Lewis, supra), boomerang DNA amplification (or "BDA")(see R. Lewis, supra); and nucleic acid hybridization (see Johnson et al., *Proc. Natl. Acad. Sci. USA,* 89, 2175, (1992)).

Standards containing a known number of proviral DNA sequences are useful in determining the sensitivity of proviral DNA detection techniques. The HIV cell line 8 E5, for example, is used as the standard for the detection of HIV proviral DNA. Folks et al., *J. Exp. Med.*, 164, 280 (1986); U.S. Pat. No. 4,752,565. The cells of the present invention contain a single copy of proviral DNA, and thus are suitable for use in preparing such standards, as the number of cells used in preparing a standard provides the number of proviral DNA copies in the standard.

Examples of the utility of the present invention include:

1. Use of both whole cell and supernatant preparations of $SIV_{sm}B7$ in extracting and/or purifying viral particles and/or proteins for biochemical analysis such as protein sequencing.

2. Use of purified supernatant material containing $SIV_{sm}B7$ virus particles in enzyme-linked immunosorbent assays (ELISA) or immunoblotting kits for antibody detection.

3. Use of antigenic proteins produced by $SIV_{sm}B7$ cells as viral antigen for detection of antibodies or antigens in ELISA immunoblotting kits.

4. Use of $SIV_{sm}B7$ cells as a viral antigen source for antibody or antigen detection in ELISA or immunofluorescent diagnostic kits, or in flow cytometric analytical assays.

5. Use of monoclonal antibodies which are made against $SIV_{sm}B7$ viral antigens and that react against SIV or HIV-2 antigens. $SIV_{sm}B7$ viral antigens are inoculated into mice or rats and lymphoid cells from these animals are fused with tumor cells to form stable monoclonal antibody producing hybridomas following standard techniques.

6. Use of isolated and molecularly cloned $SIV_{sm}B7$ proviral DNA in transforming lymphoid and non-lymphoid cells of different mammalian species for the constitutive production of viral proteins and viral particles.

7. Use of purified $SIV_{sm}B7$ cells or particles for inoculation of primates and other animals for vaccine development.

8. Use of $SIV_{sm}B7$ cells as target cells in cell mediated and complement mediated cytotoxicity assay systems.

9. Use of $SIV_{sm}B7$ particles to biologically modify HLA matched target cells for use in cell mediated cytotoxicity assays.

10. Use of $SIV_{sm}B7$ cells as a safe standard of cloned SIV antigen source for nucleic acid in situ hybridization and immunofluorescent antibody assays.

11. Use of $SIV_{sm}B7$ cells as a standard of sensitivity and specificity of methods (such as polymerase chain reaction) that are used for the detection of SIV genetic material in cells and other specimens.

The following examples are provided to illustrate the present invention, and should not be construed as limiting thereof. In these examples, SIV means Simian Immunodeficiency Virus; ATCC means American Type Culture Collection (Rockville, Md., USA); RT means reverse transcriptase; PBS means phosphate buffered solution; cpm means counts per minute; TCID means Tissue Culture Infective Dose; FITC means Fluorescein Isothio cyanate; ID means Infective Dose; °C. means degrees centigrade; PBL means peripheral blood lymphocytes; ml means milliliter; µl means microliter; mg means milligram; µg means microgram; M means molar; mM means millimolar; and V/V means volume per volume.

EXAMPLE 1

Materials and Methods viruses: Two strains of $SIV_{sm}$ were used: $SIV_{sm}H3$, a molecular clone obtained from $SIV_{sm}F236$ (Hirsch et al., *J. Med. Primatol.* 18, 279 (1989)), and $SIV_{sm}/E660$, isolated from the spleen cells of a rhesus macaque that died of SIV-induced AIDS (Hirsch et al., *J. Infect. Dis.* 163, 976 (1991)).

Cells. CEMX174 cells (American Type Culture Collection (ATCC), Rockville, Md., U.S.A, CRL 11393), were utilized. Hoxie et al., *J. Virology,* 62, 2557 (1988). CEMX174 cells were tested (at ATCC) for mycoplasma every six months. GCT cells (of a human fibrous histiocytoma cell line, ATCC catalog No. TIB 223) were cultured, and conditioned medium from the GCT cells was used for the establishment and maintenance of primary macrophage cultures (see below).

Growth of Stock Viruses: Viruses were grown and titered in CEMX174 cells. The titers of the stock viruses were $10^{3.8}$ $TCID_{50}$/ml ($SIV_{sm}H3$) and $10^{4.4}$ $TCID_{50}$/ml ($SIV_{sm}/E660$).

Generation of $SIV_{sm}$ chronically infected cell lines: About $3 \times 10^6$ CEMX174 cells were resuspended in 1 ml of stock virus. After 1 hour of incubation at 37° C., cells were centrifuged, washed with PBS (phosphate buffer saline), and resuspended at a concentration of $1.5 \times 10^5$ cells/ml in RPMI 1640 medium (Gibco, Grand Island, N.Y.) supplemented with 10% heat-inactivated fetal calf serum, penicillin and streptomycin (complete RPMI medium). Cells that survived the virus-induced cytopathic effects were passaged for two months. Cells were then plated into 96-well flat-bottom microtiter plates (Costar, Cambridge, Mass. USA) at a cell density of 1 viable cell per well. After three weeks of cultivation, individual wells containing clumps of live cells were visualized. Cells were obtained from individual wells of microtiter plates that showed cell growth in less that 30% of the wells. The techniques used were standard techniques used in hybridoma technology to clone cells.

$SIV_{sm}$ chronically infected cells were identified with the number of the individual well from which they were collected. Cells collected from well B7 were named clone B7 cells. The virus produced by the B7 cells is referred to as $SIV_{sm}B7$ virus.

The individual clones of chronically infected cells were expanded and tested for the presence of $SIV_{sm}$ nucleic acid and antigens (as described in Examples 5 and 6, below).

Cell-free supernatants: Cell-free supernatants were obtained as follows. Cells (clones or SIV-infected CEMX174 cells) were spun down at low speed (900 times gravity force) for 10 minutes. The resulting supernatant was filtered through a 0.2 micron filter and analyzed for either reverse transcriptase activity or infectivity.

EXAMPLE 2

Infection of Monocyte-derived Macrophage Cultures

PBLs from HIV seronegative individuals and from naive rhesus macaques were obtained by gradient centrifugation, using lymphocyte separation medium (Organon-Technica, Durham, N. C. USA) and heparinized blood. Macrophage cultures were grown in a 12-well plate (Costar, Cambridge, Mass. The adherent cells (about $1\times10^6$ cells/well) were washed, and duplicate wells were infected with 0.3 ml of the following cell-free virus preparations: $SIV_{sm}H3$ ($3\times10^3$ $TCID_{50}$; 0.5 µg of SIV p27); $SIV_{sm}E660$ ($3\times10^3$ $TCID_{50}$; 2.6 µg of SIV p27); or $SIV_{sm}B7$ (1.2 µg of SIV p27). After 1 hour at 37° C. under a $CO_2$ atmosphere, the cells were washed five times with 3 ml of PBS and grown in complete RPMI 1640 medium supplemented with 5% pooled AB-normal human serum, 100 U/ml penicillin, 100 µg/ml streptomycin, 2 mM glutamine and 30% of conditioned medium from GCT cells. Cell-free supernatant samples were obtained biweekly for a period of 50 days. Samples were stored at −70° C. until assayed for SIV p27 production as described in Examples 5 and 6, below. Mock-infected cells were used as controls.

EXAMPLE 3

Infection of Peripheral Blood Mononuclear cells

PBLs were obtained from heparinized blood from HIV seronegative individuals and from naive rhesus macaques, by gradient centrifugation using lymphocyte separation medium (Organon-Technica, Durham, N.C., USA). Lymphocytes ($2\times10^6$ cells/ml) were resuspended in RPMI 1640 medium containing 10 µg/ml phytohemagglutinin-P. After 72 hours in culture, $5\times10^6$ phytohemagglutinin-stimulated cells were incubated for 1 hour with 0.2 ml of either $SIV_{sm}H3$, $SIV_{sm}E660$ or $SIV_{sm}B7$. Cells were then washed twice with PBS, resuspended in complete RPMI 1640 medium containing 10% (V/V) Interleukin-2, and seeded into 48 well plates ($2\times10^6$ cells/well). Twice weekly during the incubation period of 30 days, cell free supernatant samples were obtained and were stored frozen (−70° C.) until assayed for SIV p27 antigen production. Uninfected PBLs were used as controls.

EXAMPLE 4

Analytical Methods

Antigen capture assays The SIV p27 detection kit from Coulter Immunology (Hialeah, Fla., USA) was used to quantitate the amount of virus p27 gag protein in cell-free supernatants.

Cell surface expression of $SIV_{sm}$ antigens: $SIV_{sm}$ chronically infected clones and uninfected CEMX174 cells were incubated with serum obtained from an $SIV_{sm}E660$-infected macaque. Cells were washed, incubated with FITC-labelled goat anti-human IgG and fixed with paraformaldehyde. The preparations were analyzed for intensity of fluorescence by flow cytometry using an EPICS 541 flow cytometer (Coulter Electronics, Hialeah, Fla., USA).

Reverse transcriptase (RT) assays RT activity was measured as has been previously described by S. Goldstein et al., *J. AIDS* 3, 98 (1990).

SDS-PAGE and Western blotting: Viral antigens for Western blotting were prepared using ultracentrifuged, cell-free supernatants obtained either from CEMX174 cells infected with the stock viruses, or from individual $SIV_{sm}$ chronically infected clones as described in Example 1.

Polyclonal sera and Monoclonal antibodies. The following monoclonal antibodies were used: KK59 (anti p17), KK62 (anti p27), KK41 (anti gp41), and KK13 (anti gp120). See Kent et al., AIDS, 5, 829 (1991); Kent et al., *AIDS Res. Human Retroviruses*, 8, 1147 (1992).

Antigens: Detection of antigens was performed using anti HIV-2 protease and rabbit anti p14 (vpx). See Henderson et al., Science 241, 199 (1988); Copeland et al., *Gene Anal. Tech.* 5, 109 (1988). Sera from rhesus macaques infected with $10^3$ $TICD_{50}$ of $SIV_{sm}$ E660 were obtained in our laboratories. All sera were used at concentrations of 1:100 to 1:200 in immunoblots.

PCR: SIV-specific nucleotide sequences in genomic DNA obtained from cell cultures were amplified by the polymerase chain reaction (PCR) technique, using oligonucleotide primers derived from the $SIV_{sm}H4$ long terminal repeat (LTR) genome region. The nucleotide sequences of primers, as well as the position of the 5'nucleotide in the complete $SIV_{sm}H4$ sequence (given in parenthesis) were as follows:

LTR outer forward, (521) 5'-CTCTGCGGAGAG-GCTGGC-3', (SEQ ID NO: 1);

LTR outer reverse, (776) 5'-GGGTCCTAACAGAC-CAGG-3', (SEQ ID NO: 2 );

LTR inner forward, (540) 5'-GATTGAGCCCTGG-GAGGT-3', (SEQ ID NO: 3 );

LTR inner reverse, (730) 5'-ACCAGGCGGCGAC-TAGGA-3', (SEQ ID NO: 4 ).

The first round of amplification was carried out in reaction mixtures containing Tris-CHl (10 mM); genomic DNA (0.5 µg); the pair of outer primers (10 pmol each); 200 µM each of dATP, dCTP, dGTP, dTTP; 50 mM KCl; 2 mM $MgCl_2$; and 2.5 units of Taq polymerase, in a total volume of 100 µl at pH 8.3. Amplification cycles (n=30) were carried out using a Perkin-Elmer thermal cycler (Perkin-Elmer) programmed as follows: 94° C. for 1 minute; 55° C. for 1 minute; and 72° C. for 0.5 minute. The second round of amplification was carried out in the reaction mixtures described above, except that genomic DNA and the pair of outer primers were omitted and were replaced with 10 µl of the first amplification product and the pair of inner primers (10 pmol each). The same amplification program was used for the second round. Amplification products were electrophoresed in 1% agarose gels, transferred to nitrocellulose membranes, and hybridized with a $^{32}$p-labelled probe. The unlabelled double-stranded DNA probe was synthesized by PCR amplification of a region of $SIV_{sm}H4$ LTR (see Johnson et al., *Proc. Natl. Acad. Sci. USA*, 89, 2175 (1992)), positioned inside the inner primers described above (nucleotides 559 to 712). The probe was radiolabelled by the random primer method (Amersham Corp., Arlington Heights, Ill., USA). The hybridization reaction was carried out in 10 ml of 6× Denhardt's solution (1× Denhardt's solution is 0.02% polyvinylpyrrolidone, 0.02% Ficoll, 0.02% bovine serum albumin), 6× standard saline citrate (SSC) (1× SSC is 0.15M NaCl, 0.015M sodium citrate, pH 7.4), 0.1% SDS, 0.1 mg/ml salmon sperm DNA and $5\times10^6$ cpm of the labelled probe. After 15 hours at 42° C. the membrane was washed extensively with 2× SCC and 0.1% SDS, and exposed overnight to X-ray film with an intensifying screen at −70° C. The presence of a band of 190 base pairs was determined.

Electron Microscopy. Cell suspensions were fixed in a 0.1M cacodylate buffered mixture of 2% paraformaldehyde, pH 7.3. Cells were washed in 0.1M cacodylate buffer and suspended in warm 2% agarose. Agarose embedded cell pellets were post-fixed 1 hour in 1% osmium tetroxide in 0.1M cacodylate buffer, dehydrated in a graded ethanol series and embedded in EMbed 812/Araldite 502. Thin sections were stained with aqueous uranyl acetate and lead citrate and viewed in a transmission electron microscope.

EXAMPLE 5

Establishment and Characterization Of Cells Chronically Infected with SIV: Seed Cultures and Clones Thereof After infection with either $SIV_{sm}H3$ or $SIV_{sm}/E660$, CEMX174 cells showed cytopathic changes. However, some cells survived infection and started to proliferate, and two cell lines (one infected with $SIV_{sm}H3$ and one infected with $SIV_{sm}/E660$) were obtained. These chronically infected cell lines are referred to as seed cultures. Both the $SIV_{sm}E660$ seed culture and the $SIV_{sm}H3$ seed culture have been continuously grown in culture for more than 18 months. PCR analysis revealed the presence of SIV DNA in the two seed cultures (data not shown). Two months after cultivation, both seed cultures were cloned by limited dilution. A total of 25 single-cell derived clones were obtained, and these clones have been grown in culture for more than one year.

Cell-free supernatant was obtained from 14 of the individual clones and tested for viral reverse transcriptase (RT) activity, SIV antigen production, and in vitro infectivity. Individual cells from these 14 clones were also tested for syncytia formation with CEMX174 cells. Table I shows the RT activity and SIV p27 production of cell-free supernatants obtained from some of these clones. Clones B10, F8, F11 and G6 came from $SIV_{sm}E660$ infected cells; the remaining cultures came from $SIV_{sm}H3$ infected cells.

As shown in Table I, the majority of these clones expressed low levels of RT activity. Clones derived from the $SIV_{sm}H3$ seed culture had RT levels ranging from 0.7% to 28% of that obtained with the parent seed culture. This reduction in RT activity was not due to the presence of nuclease in the media, as the same levels of RT activity were obtained with a cell-free $SIV_{sm}H3$ virus preparation which was diluted 1:1 with either tissue culture medium or with cell-free supernatants obtained from clone B7 or G9 (data not shown). One clone (B-10) had significantly higher RT activity than the $SIV_{sm}/E660$ seed culture from which it was originated. All cell-free supernatants, with the exception of clone F11, expressed the SIV p27 antigen. Moreover, SIV antigens were detected on the cell surface of all of the seven tested clones, including F11 (Table II).

Cell clones were examined for the amount of SIV p27 in cell-free virus preparations. Results indicate that all cell clones tested, except for clone F8, produced high quantities of $SIV_p27$. TABLE I.

TABLE I

| Clone | RT Activity (%) | p27 (ug/ml) |
|---|---|---|
| $SIV_{sm}H3$ s.c. | 7,813 (100) | 8.2 |
| B7 | 571 (7.3) | 8.4 |
| B8 | 56 (0.7) | 7.2 |
| C7 | 827 (10.5) | 15.0 |
| C9 | 584 (7.4) | 11.3 |

TABLE I-continued

| Clone | RT Activity (%) | p27 (ug/ml) |
|---|---|---|
| C10 | 2,148 (27.5) | 26.7 |
| D10 | 298 (3.8) | 3.3 |
| E8 | 1,626 (20.8) | 17.1 |
| E11 | 320 (4.1) | 7.5 |
| F9 | 345 (4.4) | 6.5 |
| G9 | 183 (2.3) | 8.2 |
| $SIV_{sm}E660$ s.c. | 12,548 (100) | 0.93 |
| B10 | 18,822 (150) | 0.125 |
| F8 | — (0) | 0.001 |
| F11 | — (0) | — |
| G6 | 117 (9) | 1.93 |

Table I: RT activity of cell-free supernatants is expressed in cpm per nanogram of SIV p27. Values between parenthesis indicate percent of RT activity over the control seed culture. (s.c. = seed culture.)

TABLE II

Expression of $SIV_{sm}$ antigens on the cell surface of chronically infected cells.

| Clones | Percent fluorescence |
|---|---|
| B-7 | 65.2 |
| G-9 | 78.6 |
| B-10 | 29.2 |
| G-6 | 29.2 |
| F-5 | 30.4 |
| F-8 | 44.5 |
| F-11 | 65.7 |
| CEMX174 (Control) | 0.57 |

Cells were incubated with a serum sample obtained from an $SIV_{sm}$ E660-infected macaque. Percent fluorescence was determined by flow cytometry.

The two seed cultures and the individual clones B7 and G9 were tested for cell surface $CD_4$ expression, syncytia formation, and infectivity. These cell cultures were found to be phenotypically $CD_4$ negative (data not shown). Consistent with this observation, these SIV chronically infected cells formed syncytia, but only if co-cultivated with uninfected $CD_4+$ cells (data not shown). Syncytia were first observed after 4 hours of co-cultivation and reached a maximum at 48 hours. However, syncytia formation did not correlate with virus production: the same levels of RT activity (almost equal to background levels) were obtained when either B7 or G9 clones were cultivated alone or in the presence of CEMX174 cells at a ratio of 1:2. In addition, co-cultivation of these $SIV_{sm}H3$-derived clones (B7 and G9) with either Hut-78, MT4, SupT-1, MolT-4, H-9, or $CEM_{ss}$ cells did not result in virus production or in increased RT activity (data not shown). As expected, the control $SIV_{sm}H3$ seed culture showed syncytia formation as well as high levels of RT activity after co-cultivation with CEMX174 cells (data not shown). Syncytia formation was inhibited by dextran sulfate, ($ID_{50}$=1 μg/ml; not shown), a sulfated polysaccharide that interferes with the binding of the virus envelope protein to the cellular $CD_4$receptor. See Baba et al., Proc. Natl. Acad. Sci. USA 85, 6132, 1988.

Cell-free supernatants obtained from clones B7 and G9 (i.e., $SIV_{sm}B7$ and $SIV_{sm}G9$) were tested for their ability to infect CEMX174 cells, as well as primary PBLs and macrophages from both humans and monkeys. The stock viruses ($SIv_{sm}H3$ and $SIV_{sm}/E660$) replicated in CEMX174 cells, as well as in PBL and in macrophage cultures obtained from both human and monkey species (Table III); virus replication was readily detected on or before 10 days post infection. Syncytia formation was observed in CEMX174 and in macrophage cultures infected with the stock viruses.

Figure 1:
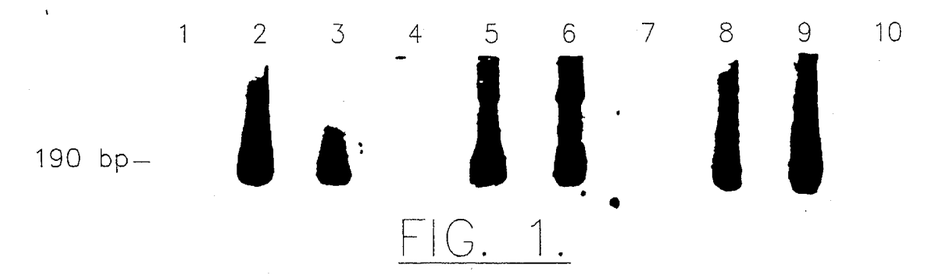
FIG. 1 Nested PCR and Southern blot hybridization of cellular genomic DNA, indicating a lack of detection of SIV LTR DNA sequence in human and in monkey periphyeral blood lymphocytes (PBL) infected with cell-free $SIV_{sm}B7$ virus. Lane 1: uninfected rhesus PBL; Lanes 2 and 3: rhesus PBL infected with $SIV_{sm}/E660$; Lane 4: rhesus PBL infected with clone $SIV_{sm}B7$; Lanes 5 and 6: rhesus PBL infected with $SIV_{sm}H3$; Lane 7: uninfected human PBL; Lane 8: human PBL infected with $SIV_{sm}/E660$; Lane 9: human PBL infected with $SIV_{sm}H3$; Lane 10: human PBL infected with $SIV_{sm}B7$.

However, neither syncytia formation nor virus replication was detected in any of the cultures infected with cell-free supernatants obtained from clones B7 or G9. PCR experiments were performed to determine whether lack of infectivity correlated with lack of viral DNA synthesis. DNA extracted from the infected cultures was amplified using nested LTR primers (see Example 4). SIV DNA sequences were detected in PBLs infected with either SIV$_{sm}$H3 or SIV$_{sm}$/E660 (FIG. 1). However, no SIV DNA sequences were detected either in PBL macrophages or in CEMX174 cells infected with cell-free B7 (or G9) viruses (Table III, FIG. 1, and data not shown).

observed.

Monoclonal antibody KK62 (anti p27) (Lane A, FIG. 2) reacted with SIV$_{sm}$H3 p27 and showed a weak reaction to SIV$_{sm}$H3 p57. Monoclonal antibody KK59 (anti p17) (Lane B, FIG. 2) reacted with SIV$_{sm}$H3 p16, and weakly with SIV$_{sm}$H3 p57. However, these monoclonals strongly reacted to a broad (50–67 kD) SIV$_{sm}$B7 band, and recognized several SIV$_{sm}$B7 proteins which were not present in the mature SIV$_{sm}$H3 particles. Reactivity of KK62 and of KK59

TABLE III

| | Infectivity of Individual Cell-Free Virus Clones | | | | | | | | | |
|---|---|---|---|---|---|---|---|---|---|---|
| | CEMX174 | | H/PBL | | H/Mφ | | M/PBL | | M/Mφ | |
| Clone | RT | PCR | P27 | PCR | P27 | PCR | P27 | PCR | P27 | PCR |
| SIV$_{sm}$H3 (stock virus control) | + | + | + | + | + | + | + | + | + | + |
| SIV$_{sm}$E660 (stock virus control) | + | N.D | + | N.D | + | + | + | + | N.D | N.D |
| SIV$_{sm}$H3 seed culture | + | + | N.D | N.D | N.D | N.D | N.D | N.D | N.D | N.D |
| Clone B7 | − | − | − | − | − | − | − | − | − | − |
| Clone G9 | − | − | − | − | − | − | − | − | − | − |

Cultures were infected with cell-free supernatants obtained from the individual clones.
H = Human; M = Monkey; PBL = peripheral blood lymphocytes; Mφ = macrophage; N.D. = not done;
(−) = Lack of RT activity or p27 production 30 and 50 days after infection; no detection of viral DNA synthesis using PCR amplification.*
(+) = RT activity or p27 production detected; viral DNA synthesis detected using PCR amplification.*
*"Nested" PCR amplification was performed using SIV LTR primers.

The above results describe the isolation and partial characterization of virus particles produced by SIV$_{sm}$ chronically infected cells. CEMX174 cells that survived SIV$_{sm}$ infection were phenotypically CD4− and produced infectious, as well as non-infectious virus particles. Lack of expression of the cellular CD4-antigen has been observed previously in cells persistently infected with HIV. Surviving cells may represent an outgrowth of CD4−cells that were originally present in the CEMX174 culture. Therefore, the isolated SIV$_{sm}$ chronically infected cells may consist of different CD4−cell populations. Single cell clones obtained from these cultures were also found to be phenotypically CD4− and did not revert to the CD4+ phenotype during a 12 month observation period (data not shown). These clone cells (B7 and G9) were undistinguishable by morphology and growth characteristics from uninfected CEMX174 cells (data not shown). SIV chronically infected clones B7 and G9 formed syncytia, but only when co-cultivated with CEMX174 cells, however, syncytia formation did not result in infectious virus production.

EXAMPLE 6

Viral Antigens in Particle-Associated Material from Clone B7

Figure 2:
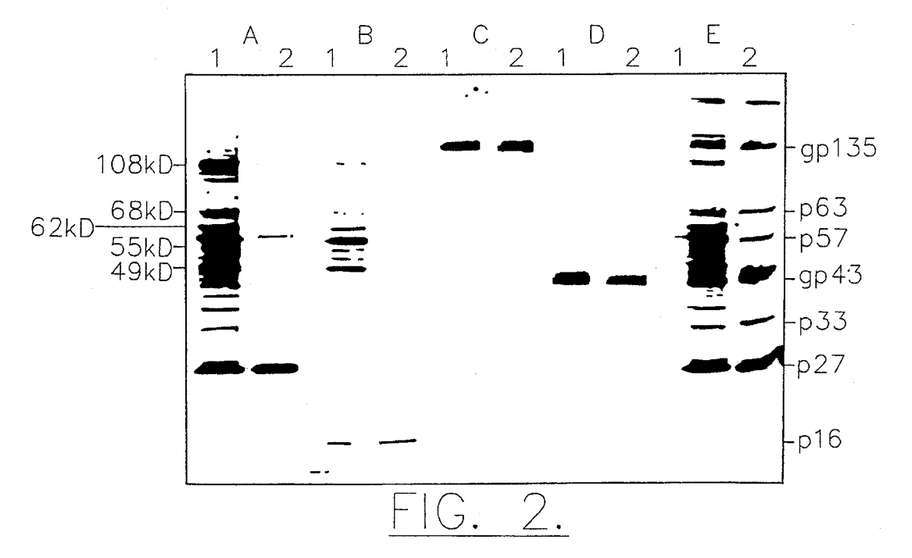
FIG. 2: Western blot analysis of $SIV_{sm}B7$ (Lanes 1) and $SIV_{sm}H3$ (Lanes 2) by monoclonal antibodies (MAbs). Virus preparations were electrophoresed through a 10% acrylamide gel, transferred to nitrocellulose membranes and probed with either the indicated MAbs or with serum from an $SIV_{sm}/E660$-infected rhesus macaque. Lane A: MAb.KK62 (anti p27); Lane B: MAb.KK59 (anti p17); Lane C: MAb.KK13 (anti gp120); Lane D: MAb.KK41 (anti gp41); and Lane E: serum from an $SIV_{sm}/E$ 660 -infected rhesus macaque. The obtained molecular weights (MW) of $SIV_{sm}H3$ proteins are indicated at the right of the Figure; MW of some of the $SIV_{sm}B7$ protein bands not present in the $SIV_{sm}H3$ preparations are shown at the left of the figure.

The presence of viral antigens in cell-free pelleted supernatants obtained from clone B7 was determined by immunoblotting, using polyclonal as well as monoclonal antibodies. FIG. 2 (Lane E) and FIG. 4 (Lane C) show that serum from an SIV$_{sm}$/E660-infected rhesus macaqae recognized the following SIV$_{sm}$H3 viral proteins in cell free supernatants of clone B7: gp 135 (EM) , p68 (RT), p57 (gag precursor), gp43 (TM) , p33 (integrase), p27 (gag), p16 (gag), p14 (vpx), p11 (protease) , p8 (gag), and p6 (gag) . FIG. 2 shows that B7 particles contained structural proteins (p57, p27, p16 and env) recognized by the reference macaque serum. Other protein bands, not present in the mature SIV$_{sm}$H3 particles, were also observed. They included bands of the following MW: 108, 62, 55, 52, 49, 36, and 32 kD. The reference serum (Lane E, FIG. 2) weakly stained B7 p68/66 proteins, and did not reveal a SIV$_{sm}$B7 p33 protein band. A broad SIV$_{sm}$B7 band at 60–57 kD was to protein bands present in the molecular weight range of 130–160 kD was also observed. (FIG. 2).

FIG. 2 also shows the reactivity of monoclonals KK13 (anti gp120) (Lane C, FIG. 2), and KK41 (anti gp41) (Lane D, FIG. 2), to particle-associated SIV$_{sm}$H3 and SIV$_{sm}$B7 antigens. The monoclonal antibody to the external glycoprotein gp 120 (KK13) reacted with a band at 135 kD which was present in SIV$_{sm}$B7 as well as in SIV$_{sm}$H3 antigen preparations. We identified this band as gp135, the external virus envelope glycoprotein. Monoclonal KK41 revealed a prominent band at 43 kD, and showed some reactivity to bands at 130, 68 and 57 (FIG. 2) in SIV$_{sm}$B7 as well as in some SIV$_{sm}$H3 antigen preparations. The prominent band at 43 kD was identified as the transmembrane glycoprotein gp43. The 130 kD band may represent gp43 trimmers. See Orange et al., Nature, 342, 1989. The significance of the bands at 68 kD and at 47 kD is not clear. They may represent dimers of a truncated transmembrane protein.

Figure 3:
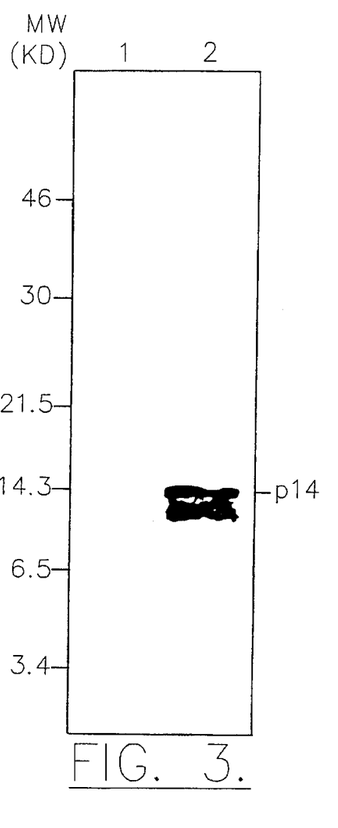
FIG. 3: Immunoblot analysis of $SIV_{sm}B7$ (Lanes 1) and of $SIV_{sm}H3$ (Lanes 2) viral proteins separated by 15% SDS-PAGE, transferred to nitrocellulose membranes, and probed with anti-vpx rabbit serum; showing lack of vpx detection in $SIV_{sm}B7$ virus preparations.
Figure 4A:
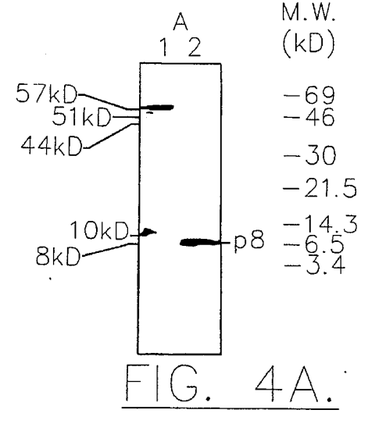
FIG. 4: Detection of viral protease and gag p8 antigens by Western blots. $SIV_{sm}B7$ (Lanes 1) and $SIV_{sm}H3$ (Lanes 2) proteins were separated by 15% acrylamide gels and transferred to Immobilon-P membranes (Millipore Corporation, Bedford, MA 01730). Lane A: rabbit antiserum to purified SIV/Mne p8; Lane B: rabbit antiserum to synthetic HIV-2 protease; Lane C: serum from a macaque infected with $SIV_{sm}E660$.
Figure 4B:
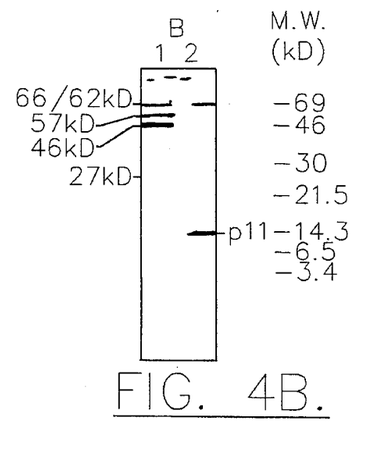
Figure 4C:
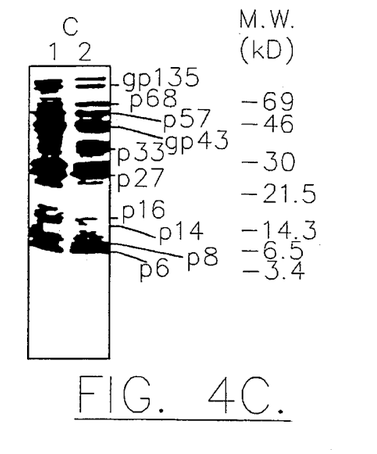

FIG. 3 shows the reactivity of anti p14 (SIV vpx) polyclonal rabbit sera with SIV$_{sm}$B7 and SIV$_{sm}$H3 antigens; vpx was not detected. Lane A of FIG. 4 shows that anti-p8 polyclonal sera detected SIV$_{sm}$p8 and that this serum stained several SIV$_{sm}$B7 bands, including p8.

In SIV$_{sm}$B7 immunoblots, the very prominent band at 60–57 kD as well as the unusual proteins detected by the gag monoclonals suggest that the B7 clone virus may be defective in proteolytic processing. To determine the presence of the viral protease in SIV$_{sm}$B7 particles, immunoblots were developed with anti HIV-2 protease serum (see Example 4). Lane B of FIG. 4 shows that anti HIV2 protease serum recognized SIV$_{sm}$H3 protease (p11) and that it strongly reacted with two SIV$_{sm}$B7 protein bands at 57 kD and at 46 kD.

Figure 5A:
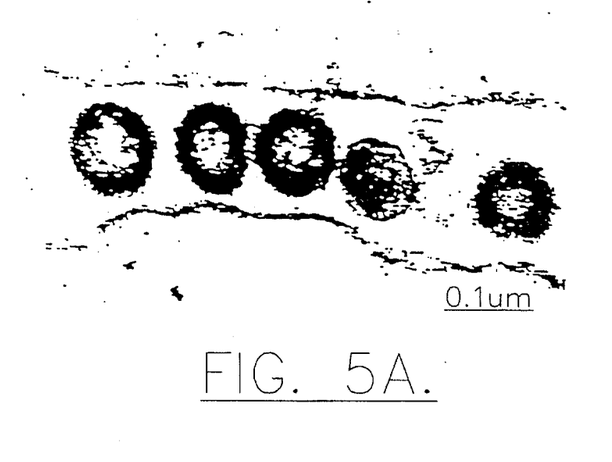
FIG. 5A shows budding virus particle at the plasma membrane of a cell from clone B7.
Figure 5B:
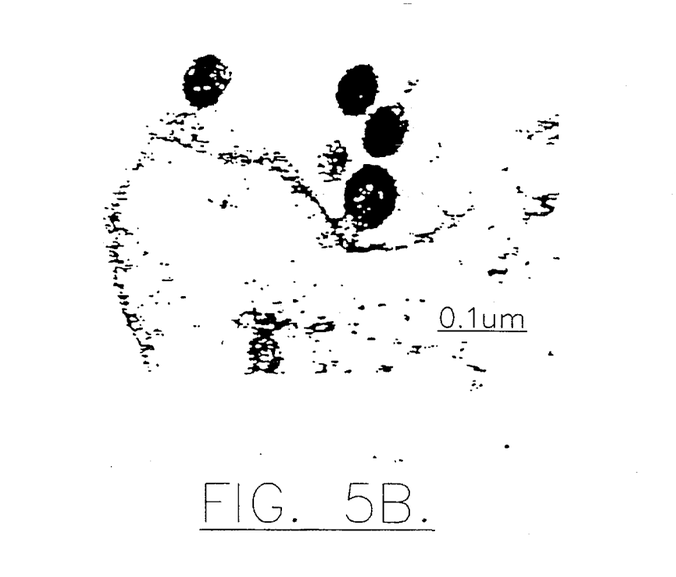
FIG. 5B shows immature extracellular virus particles between cells from clone B7.

Electron microscope analysis of clone B7 chronically infected cells revealed the presence of large quantities of enveloped, but immature, lentivirus particles (FIG. 5). Enveloped but immature lentivirus particles characteristically have an electronlucent center, and lack the eccentric electron-dense core seen in mature lentivirus particles.

Immunoblot analysis of particle-associated material produced by clone B7 revealed the absence of integrase (p33) protein, which is required for virus replication. In addition, low levels of p68 (RT) were detected. The presence of the envelope proteins gp135 and gp43 in $SIV_{sm}B7$ virus suggests that the inability of $SIV_{sm}B7$ virus to replicate may be due to factors that occur after $SIV_{sm}B7$ virus penetration into susceptible cells. Kraiselburd et al, Abstract No. 225; poster session A33, PO-A33; IX International Conference on AIDS, Berlin, Germany, Jun. 7–11, 1993. The absence of the integrase protein and the low levels of RT activity detected in $SIV_{sm}B7$ particles may explain the lack of both infectious virus production and vital DNA synthesis in CD4+ cells incubated with $SIV_{sm}B7$ virus preparations.

The studies described above show that monoclonal antibodies against the mature gag proteins (p27 and p16) reacted with several $SIV_{sm}B7$ protein bands in the range of MW 27 kD to 160 kD. In addition, both monoclonals individually reacted to p27 and to p16. The large MW proteins found in clone B7 may represent unprocessed cleavaged products of the gag-pol fusion polyprotein, and therefore the $SIV_{sm}B7$ particles would contain large amounts of the p57 gag precursor as well as gag products not present in $SIV_{sm}H3$ virus preparations. The B7 particles also contained mature gag proteins of the expected molecular weights (p27, p16, p8 and p6). Therefore, the $SIV_{sm}B7$ gag precursor was not blocked to proteolysis. However, very little if any free protease (p11) was detected in $SIV_{sm}B7$ particles.

Vpx was not present in detectable amounts in $SIV_{sm}B7$ particles. This protein has been shown to be incorporated into virions, but is not essential for infectivity. See, e.g., Henderson et al., Science 241, 199 (1988); Vaishnav and Wong-Staal, *Ann. Rev. Biochem.*, 60, 577 (1991). Lack of pol and vpx gene products strongly suggest that the provirus(es) present in $SIV_{sm}B7$ cells had multiple genomic defects.

There was clearly a defect in the proteolytic processing of the $SIV_{sm}B7$ virus proteins. However, other defects may contribute to the overproduction of gag and gag-pol precursors and to the absence of detectable pol and vpx gene products.

These data show that $SIV_{sm}B7$ viruses lack critical gene products required for virus maturation and infectivity. No virus reversion was observed after more than a year of continuous in vitro cultivation of $SIV_{sm}B7$ cells, indicating that the resident $SIV_{sm}B7$ provirus contains stable mutations leading to multiple functional defects.

EXAMPLE 7

Antibodies to $SIV_{sm}H3$ Induced in Rabbits and in Mouse Inoculated with cell-free $SIV_{sm}B7$ Virus One Balb/c mouse and two New Zealand White (NZW) rabbits (housed under BL-3 conditions), were inoculated with cell-free, ultracentrifuged $SIV_{sm}B7$ virus preparations. Virus antigens were emulsified in incomplete Freund's adjuvant. Each dose consisted of 200 μg of total protein in 0.2 ml of PBS:adjuvant (1:1). Immunizations were performed on days 0, 35, 48, and 69. Sera obtained from these animals on day 75 showed reactivity to the following $SIV_{sm}H3$ proteins: gp135 (weak reaction); p57, gp43, p27, p17 and p8 (data not shown).

Figure 6:
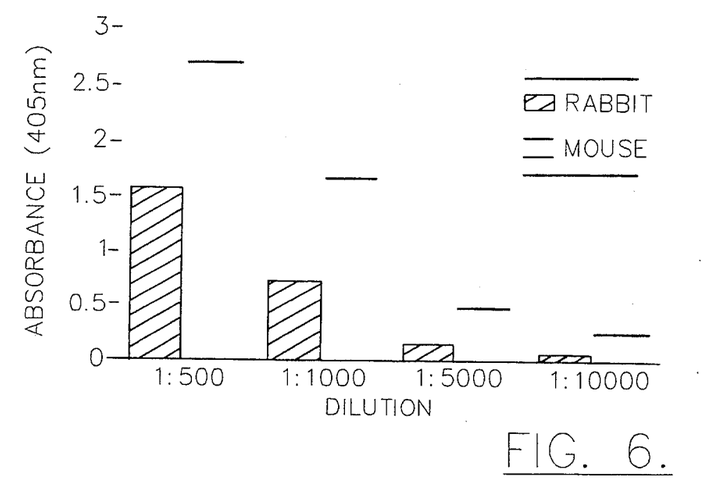
FIG. 6: ELISA assay using serum samples from animals inoculated with cell-free clone B7 preparations, and reacted with recombinant $SIV_{mac}239$ gp130; sera from clone $SIV_{sm}B7$ immunized animals had high antibody titers against recombinant $SIV_{gp}130$.

Binding to recombinant gp130: Serum samples obtained from the immunized animals were allowed to react to recombinant $SIV_{mac}239$ gp130, in an ELISA assay. Results are shown in FIG. 6. It can be seen that sera from $SIV_{sm}B7$ immunized animals had high antibody titers against recombinant $SIV_{gp}130$.

$SIV_{sm}H3$ neutralizing antibodies induced by $SIV_{sm}B7$ virus: Sera obtained from the immunized animals were heat-inactivated (56° C. for 30 minutes), and serially diluted in RPMI 1640 medium containing 10% fetal calf serum. $SIV_{sm}H3$ (about 80–100 syncytium forming units in 50 microliters) was incubated with 100 μl of each serum dilution for 30 minutes at 37° C., in microtiter wells coated with polylysine. After this incubation period, 50 μl of CEMX174 cells ($1.5 \times 10^6$ cells/ml) were added to each well. The 96 well microtiter plate was incubated at 37° C. under $CO_2$ for 48 hours. Syncytia were read with the aid of an inverted microscope. The percent inhabitation of syncytia was determined for each serum dilution. The serum neutralizing titer is expressed as the reciprocal of the dilution that inhibited 50% of $SIV_{sm}H3$-induced syncytia. Results obtained are shown in Table IV.

TABLE IV $SIV_{sm}H3$ neutralizing antibodies induced by $SIV_{sm}B7$ virus

| Immunized animal | N.A. titers Pre | N.A. titers Day 75 |
|---|---|---|
| Mouse 1 | <60* | 3,840 |
| Rabbit 1 | <60 | 960 |
| Rabbit 2 | <60 | 1,400 |

*Lowest dilution used in the test.
N.A. = neutralizing activity

From these data, it can be concluded that the $SIV_{sm}B7$ immunized animals produced antibodies that neutralized $SIV_{sm}H3$-induced syncytia formation.

EXAMPLE 8

Adsorption of Serum Neutralizing Activity by $SIV_{sm}H3$-infected CEMX174 Cells Serum samples were obtained from the immunized animals, and 0.4 ml of either a 1:60 dilution (rabbit sera) or a 1:200 dilution (mouse sera) were incubated with either $3\times10^6$ CEMX174 cells, or $2.5\times10^6$ $SIV_{sm}$ infected CEMX174 cells. A control sample was incubated without added cells. After 18 hours of incubation at 4° C., cells were spun down, and the sera was heated at 6° C. for 30 minutes to inactivate residual virus. Sera was diluted, and incubated with $SIV_{sm}H3$, as described above. Results obtained are shown in Table V.

TABLE V

| Pre-incubation of serum with: | N.A. titers Mouse | N.A. titers Rabbit 2 |
|---|---|---|
| (Control) | 3,000 | 1,400 |
| CEMX174 cells | 3,300 | 1,400 |
| $SIV_{sm}H3$ infected CEMX174 | <200* | 60* |

*Lowest dilution used in the test.
N.A. = neutralizing activity

These data showed that the neutralizing antibodies elicited by $SIV_{sm}B7$ virus could be partially (or totally) adsorbed by $SIV_{sm}H3$-infected cells. The neutralizing activity was not adsorbed by uninfected CEMX174 cells.

The above studies illustrate that the replication-defective $SIV_{sm}H3$ virus elicited specific $SIV_{sm}H3$ neutralizing antibodies in mammals.

EXAMPLE 9

Detection of a Single copy of Integrated $SIV_{sm}$ Proviral DNA in $SIV_{sm}B7$ Cells The number and state of proviral DNA copies of $SIV_{sm}B7$ cells were analyzed by Southern blot hybridization of Eco R1-digested cellular DNA, following the protocol of Folks et al, *J. Exp. Med.*, 164, 280, (1986).

Figure 7:
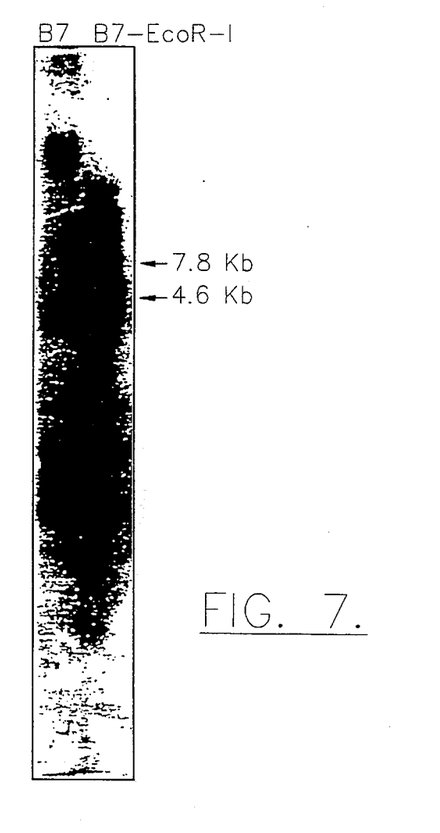
FIG. 7: Southern blot hybridization of a $^{32}p$ SIV LTR DNA probe with DNA extracted from the chronically infected $SIV_{sm}B7$ cells. One band was obtained with uncleaved (genomic) $SIV_{sm}B7$ DNA. The probe hybridized with two ECO R1 B7 fragments, at 7.8 Kb and 4.6 Kb.

An SIV$_{sm}$ LTR $^{32}$p labelled probe (specific activity 2×10$^9$ cpm/µg) was allowed to hybridize to either Eco R1 cleaved or uncleaved (genomic) SIV$_{sm}$B7 cellular DNA. Hybridization was carried out as described by Folks et al., *J. Exp. Med.*, 164, 280 (1986). Since the parental SIV$_{sm}$H3 virus contains two internal Eco R1 restriction sites, the presence of only two reactive Eco R1 cleavage products (FIG. 7) is consistent with the clonality of SIV$_{sm}$B7 cells and with the existence of a single integrated copy of viral DNA.

The foregoing is illustrative of the present invention and is not to be construed as limiting thereof. The invention is defined by the following claims, with equivalents of the claims to be included therein.

---

That which is claimed is:

1. Non-infectious SIV viral particles produced by the cell line having ATCC accession number CRL 11393.

2. A non-infectious SIV particle produced by the cell line having ATCC accession number CRL 11393 which comprises virus proteins having molecular weights in kilodaltons of 135, 43, 27, 16 and 8 and lacks vital proteins of 14 and 33 kilodaltons.

3. A composition comprising an antigenic preparation of the SIV viral particles of claim 1.

4. A pharmaceutical composition comprising an immunogenic amount of the non-infectious SIV viral particles of claim 1 in a pharmaceutically acceptable carrier.

5. A method of inducing antibodies to SIV in a non-human mammalian subject, comprising administering to said subject an immunogenic amount of the viral particles of claim 1.

6. The method of claim 5 wherein said subject is susceptible to SIV infection.

7. The method of claim 5, wherein said antibodies are neutralizing antibodies.

8. The method of claim 5, wherein said subject is a primate.

9. A method for immunizing a, non-human subject susceptible to SIV infection against SIV infection, comprising administering to the subject an immunogenic amount of the viral particles of claim 1.

10. The method of claim 9, wherein said subject is a mammal.

11. The method of claim 9, wherein said subject is a primate.

12. A method of inducing antibodies that react with HIV-2 in a non-human mammalian subject, comprising administering to said subject an immunogenic amount of the viral particles of claim 2.

13. The method of claim 12 wherein said subject is susceptible to HIV-2 infection.

14. The method of claim 12, wherein said antibodies are neutralizing antibodies.

15. The method of claim 12, wherein said subject is a primate.

* * * * *

UNITED STATES PATENT AND TRADEMARK OFFICE
CERTIFICATE OF CORRECTION

PATENT NO.   : 5,470,572
DATED        : November 28, 1995
INVENTOR(S)  : Edmundo Kraiselburd It is certified that error appears in the above-indentified patent and that said Letters Patent is hereby corrected as shown below:

Column 3, Line 22, delete "periphyeral" and insert --peripheral--.

Column 5, Line 30, insert --the-- prior to "antigens".

Column 6, Line 49, delete "vital" and insert --viral--.

Column 16, Line 58, delete "$SIV_{sm}H3$ virus elicited" and insert --$SIV_{sm}B7$ virus elicited--.

Signed and Sealed this

Twenty-fifth Day of June, 1996

Attest:

BRUCE LEHMAN

*Attesting Officer*    *Commissioner of Patents and Trademarks*